United States Patent [19]

Natitus et al.

[11] 4,298,863
[45] Nov. 3, 1981

[54] PORTABLE PATIENT CALL

[75] Inventors: Donald P. Natitus, Aurora; Curt T. Carlson, Denver, both of Colo.

[73] Assignee: St. Anthony Hospital Systems, Denver, Colo.

[21] Appl. No.: 117,615

[22] Filed: Feb. 10, 1980

[51] Int. Cl.³ .......................... G08B 21/00; A61B 5/10
[52] U.S. Cl. ..................................... 340/573; 128/782; 340/626; 340/825.19; 340/825.36; 200/83 R
[58] Field of Search ............... 340/611, 614, 626, 311, 340/330, 573; 128/721, 782; 200/51 R, 81 H, 83 R

[56] References Cited

U.S. PATENT DOCUMENTS

| 1,799,126 | 3/1931 | Schirmer | 200/81 H |
| 2,736,888 | 2/1956 | McLain | 340/311 X |
| 2,838,629 | 6/1958 | Panzenhagen | 200/81 H |
| 2,875,291 | 2/1959 | Armstrong et al. | 200/81 H X |
| 2,910,680 | 10/1959 | McLain | 340/311 |
| 3,104,293 | 9/1963 | Rendler | 200/51 R |
| 3,122,731 | 2/1964 | Hutchison | 340/311 |
| 3,234,739 | 2/1966 | Pierce, Jr. | 200/81 H |

FOREIGN PATENT DOCUMENTS

| 627341 | 6/1927 | France | 128/721 |
| 1480160 | 4/1967 | France | 128/721 |
| 254744 | 9/1927 | Italy | 128/721 |
| 566145 | 12/1944 | United Kingdom | 340/330 |
| 1296033 | 11/1972 | United Kingdom | 200/81 H |

Primary Examiner—John W. Caldwell, Sr.
Assistant Examiner—Daniel Myer
Attorney, Agent, or Firm—James E. Pittenger

[57] ABSTRACT

A self-contained, electrically-isolated patient call device is provided which permits use by quadriplegic or partially paralyzed patients which includes an extremely sensitive, adjustable, non-sealed, pneumatic, pressure transducer activated by the patient which in turn produces a simultaneous movement of an actuation transducer which actuates an electronic circuit. The switch and electronic circuit can produce both an audible alarm signal and activation of electrical contacts to simultaneously operate a nurse call system. The transducer activated by the patient can be actuated by a minor flexation of a muscle or skin area or can be the result of air pressure created by the breath or blowing against the transducer. This device permits electrical isolation of the patient to prevent shock and allows pneumatic activation of the system mounted directly on or close to the patient to eliminate the necessity for extended movement or positional adjustments which are usually impossible for the patient.

13 Claims, 12 Drawing Figures

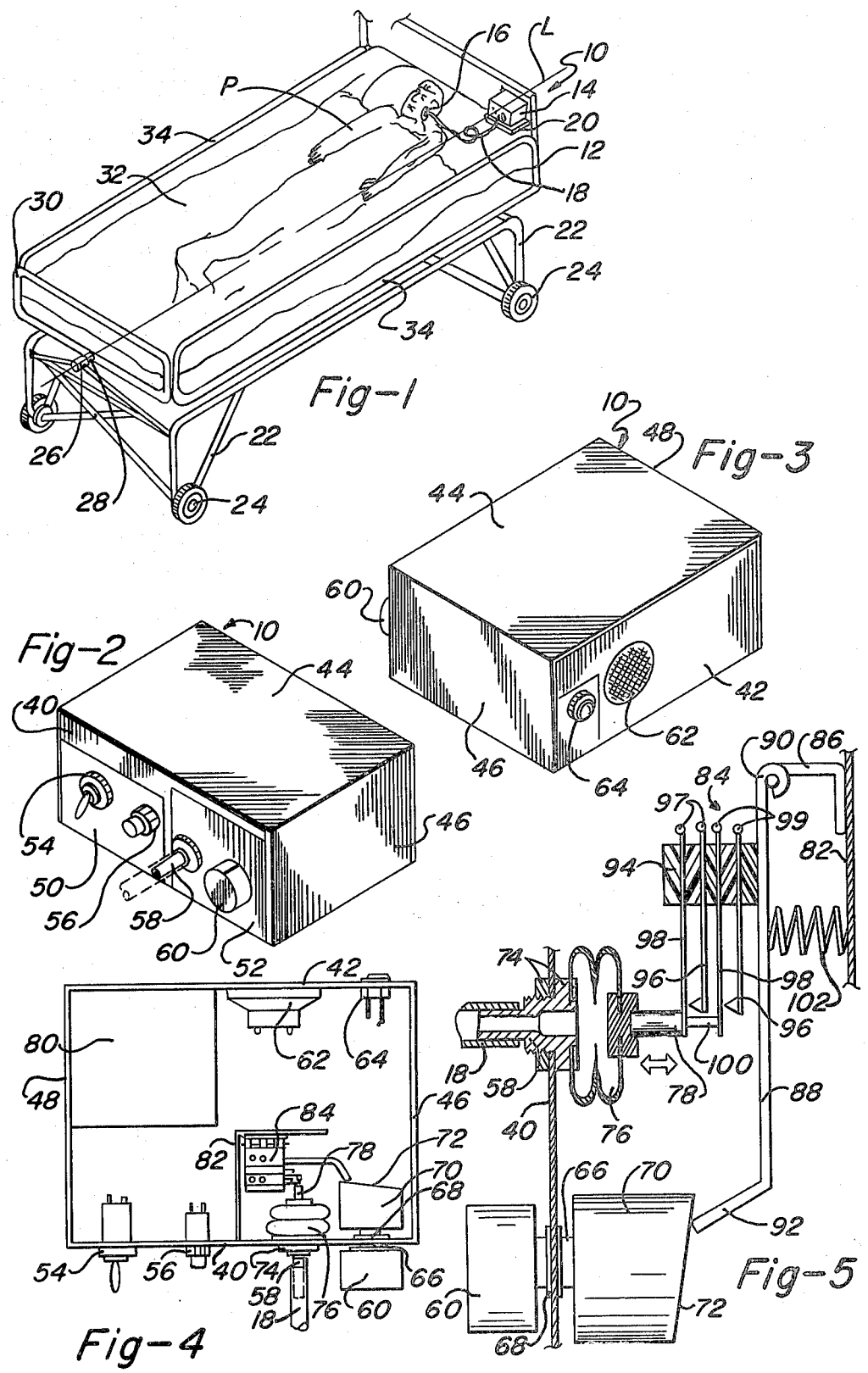

PORTABLE PATIENT CALL

FIELD OF INVENTION

This invention relates to a self-contained electrically isolated patient call system, and more specifically is directed to an extremely sensitive patient-actuated call system which can be used by quadriplegic and partially paralyzed persons.

It is naturally understood that patients who are partially paralyzed or completely paralyzed, such as quadriplegic, are very helpless and need constant attention and assistance in everyday living. Because of the problems associated with managing a patient such as this, it has been found that a patient call system which can be readily activated by the paralyzed patient be provided to assist in solving these significant problems.

Also, it is required that quadriplegic patients be rolled in a side to side or oscillating motion around the longitudinal axis of their body in order to maintain the lung tissue in a coated and moist condition. This is necessary to prevent the patients from contracting pneumonia and other respiratory problems. Because of this constant oscillating motion and the hazardous electrical atmosphere which is created by the electrically powered bed facilities, it has been found necessary to electrically isolate the patient whenever possible and still provide the necessary access to a patient call system. This oscillating motion presents a substantial problem when considering the immobility of the patient to actuate a call system.

BACKGROUND ART

The prior art patent to Rendler, U.S. Pat. No. 3,104,293, reveals a hospital call signal switch having a closed pneumatic bulb in conjunction with a moveable cylinder. Movement of the cylinder closes contacts within an electrical jack which is plugged into the conventional nurse call system. The pneumatic bulb, which is typical of most actuators provided, is said to be actuated by an elbow, knee, foot or other part of the body and essentially is provided to isolate the patient from an electrical system. This type of bulb actuated system requires considerable movement and squeezing of the bulb and a required large pressure build up in the system to actuate it. This voluntary muscular control to effectively actuate a system such as this is impossible for the paralyzed or arthritic patient.

The patent to Panzenhagen, U.S. Pat. No. 2,838,629, shows another bulb-actuated, remote switching device which provides a mechanism for latching the contacts in a closed position until the switch is reset. Multiple contacts are disclosed in this device for providing signals in one or more different locations.

The patent to Schirmer, U.S. Pat. No. 1,799,126, shows a hospital call switch having a housing which is plugged directly into a corresponding wall outlet. A conventional sealed pneumatic bulb and tube are connected to a closed diaphram chamber within the housing. This provides a closed and sealed pneumatic actuation system which is typical of all known prior art.

DISCLOSURE OF THE INVENTION

According to the present invention, a self-contained, electrically isolated, patient call system is provided which can be adjusted to operate on extremely small actuation movements and pressures. In this device, a low voltage battery energy source is provided which powers a sound producing circuit in order to obtain an alarm signal. In addition, at the same time auxiliary electrical contacts can be closed which allows the use of the device with an interconnecting cable into a conventional nurse call system. By the same token, any other type of alarm system such as a remote signaling device or a telephone automatic dialing system can be activated by the contacts.

Some of the most novel features of the invention are contained in the actuation system which is included in this invention. Although this invention can be used by any patient, even for the detection of seizures, it is primarily intended for patients with only limited or no body movement. With these types of patients, usually only facial movements such as forehead, eye or cheek movement is possible, or tongue or breath movement may be the only capability.

The actuation system, according to the present invention, includes a flexible chamber within the housing positioned in close proximity to an electrical contact actuating arm. The flexible chamber is connected to a tube by a connector mounted on the external portion of the housing. A beveled, rotatable cam is provided in contact with the actuation arm to accurately set the dimensional position of the arm in relation to the actuation surface of the flexible chamber, resulting in a variable sensitivity control. The flexible chamber is made from any material having a sufficient flexible or resilient characteristic and usually fabricated in accordion arrangement to allow movement of the end of the chamber with minute pressure increases within the chamber itself.

The patient transducer provided as part of this invention is an open device having a planar member which includes a tube connector centrally located on one surface. If desired, the transducer can be arranged in the shape of a cone with the tube connection provided at the apex. Around the outer edge of the member is provided an adhesive material or other connecting means which can hold the transducer against the patient's skin. Thus, the transducer is mounted directly on a portion of the patient's body such as a cheek, forehead, chin, or any part over which the patient has some voluntary muscular control. As another embodiment, the transducer can be supported or held in position in close proximity to the patient's lips so that merely by blowing on the open side of the open transducer, the call system can be activated.

With the patient transducer provided in the present invention, and the actuation sensitivity of the device adjusted for the particular patient, merely the moving of the surface of the cheek, forehead, or chin will be sufficient to increase the pressure within the flexible chamber of the device to actuate the contacts and the alarm system. In this way, the patient is isolated from any possible electrical shock. The positioning of the patient-actuated transducer, contrary to that previously provided in the prior art, can be mounted directly on or near to the patient so that it will move with the patient and in conjunction with any necessary oscillating or reciprocating movement without resultant false triggering.

One object of the present invention is to provide a patient call system which can be easily activated by a paralyzed or immobile patient.

Another object of the present invention is to provide a patient call device which is completely self-contained and easily and cheaply manufactured.

A still further object of the present invention is to provide a patient call system wherein the sending or patient transducer can be mounted or adhered directly to the patient's skin or body and the device is capable of being adjusted so that actuation can be accomplished by extremely small muscular movement.

Another objective of the present invention is to provide a patient call system which is portable and can be moved with the patient and yet activated at any time.

A still further objective of the present invention is to provide a battery-operated, patient call system which draws no current when in standby and thus provides greatly extended battery life.

BRIEF DESCRIPTION OF THE DRAWINGS

Other objects of this invention will appear in the following description and appended claims, reference being made to the accompanying drawings forming a part of the specification wherein like reference characters designate corresponding parts in the several views.

FIG. 1 is a perspective view of a patient lying in a hospital bed with a patient call device according to the present invention, in use;

FIG. 2 is a perspective view of the front portion of the housing of the patient call device according to the present invention;

FIG. 3 is a perspective view of the rear portion of the housing;

FIG. 4 is a top plan view of the patient call device with the top cover removed and showing the relative position of the internal components;

FIG. 5 is an enlarged pictorial, partial, sectional view of the pneumatic actuation bellows and the adjustment device for positioning the switch contacts with respect to the bellows;

DETAILED DESCRIPTION

Figure 7:
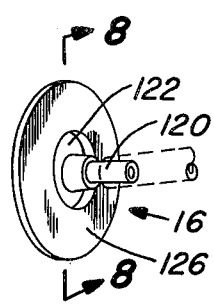
FIG. 7 is a perspective view of a patient transducer, according to the present invention, showing the hose coupling on the rear surface and a connected hose in dashed lines.

In FIG. 1 can be seen a hospital bed 12 with a patient P lying therein. Although it is intended that the present invention is to be used with quadriplegic or at least partially paralyzed patients, it is possible that the device can be used with any patient or partially immobile person, such as one suffering from chronic arthritis, in order to obtain attention or services. The patient call device 10, according to the present invention, can be suitably mounted on the bed 12 on an attached bracket or platform 20 or other support means such as a table or night stand (not shown). The battery-operated electronic actuation portion of the invention is housed in the cabinet or housing 14 and a patient-operated transducer 16 is mounted either on the patient's face or a portion of the body or mounted extremely close to the patient P. An interconnecting pneumatic tube 18 connects the housing 14 with the patient transducer 16.

One of the major attributes of the present invention 10 is its adaptability for use on a patient who is continuously rocked or in motion which is necessary to prevent internal complications. One such situation is depicted in FIG. 1 wherein the bed 12 is of the longitudinally rotating type which includes a base structure 22 having wheels 24.

The base structure 22 has a rigid framework upon which a motor and axle 26 and 28 is provided at each end. A suitable external electrical source such as 110 volts AC is provided to the motor and the controls for providing the desired motion. The upper portion of the bed 12 is a separate framework 30 for supporting the mattress 32 and side rails 34. The patient P lies on the mattress 32 usually in an immobile support (not shown) so that the patient will not generally move with respect to the upper portion of the bed 30.

In order to alleviate or prevent respiratory or circulatory problems, it is desirable to rotate the patient around the longitudinal axis shown by the line L. The axis L generally passes through the pivots for the upper bed portion 30 at both the head and foot of the bed. The motor 26 causes the upper portion 30 of the bed to rock from side to side around the axis L in order to move the patient in an oscillating manner so that the accumulation of fluids within the lungs remains minimal to prevent pneumonia and other similar internal complications.

With a bed that performs this rocking or oscillating motion, there is some hazard with respect to the electrical power connected to the bed in order to perform this function. It is highly desirable to isolate the patient as much as possible to prevent any possible chance of electrical shock. It is understood that partially paralyzed patients cannot generally feel hazardous levels of electric current and thus, would be unable to react to such possible impending danger.

For this reason, the patient call device, according to the present invention, is limited to low voltage power to prevent any possibility of electrical shock caused by the device itself. In addition, the non-conductive plastic tubing 18 provides ideal electrical isolation to the patient. Thus, the invention cannot contribute to any possible hazard which would endanger the patient's life. In addition, it is also desirable that the device be arranged so that the patient is free to be rotated.

In FIGS. 2 and 3 are shown the main portion of the device having a front panel 40 and rear panel 42. Other portions of the cabinet or housing are top 44, right side 46, and left side 48. Depending upon the structure of the cabinet, the top 44 and the bottom (not shown) can be fastened to the remaining portion of the cabinet by means of screws or other easily removable fasteners. In this way servicing for the unit can be easily provided.

On the front panel 40 are provided the electronic section 50 and pneumatic section 52. The electronic panel section 50 includes the power switch 54 and the push-type reset or test switch 56. By the same token, the panel 52 for the pneumatic section includes a hose connector 58 and a knob 60 for the sensitivity control. On the back panel 42 of the unit is provided the grill and speaker 62 and a plug or jack 64 for conecting the auxiliary switch contacts to an existing hospital patient call system. The unit, according to the present invention, is completely self-contained with all of the electrical energy power provided by an internal battery. A prototype of the present unit has been powered by a conventional 9-volt alkaline battery source, but any suitable and readily available 9-volt battery would be satisfactory. Usually a 9 volt source is desirable, but it is to be understood that any low voltage DC power source can be provided. It is also possible to use rechargeable batteries. When not being utilized on a patient, a battery charger can be plugged into a conventional wall outlet with a low voltage lead wire connected to a plug on the back panel 42 of the housing. The important aspect is that only low voltage be provided preferably with a self-contained, internal battery power source.

It is also to be understood that in conjunction with the present invention, a number of small separate batteries such as the 1.5 v DC penlight cells can be utilized with the cells connected in series to provide the desired voltage. One such arrangement would be the use of six of the penlight cells to provide a total of nine volts. This arrangement can be used for extremely long battery life. In fact with the present electrical circuits, the useful life of the battery approximates its shelf life.

FIG. 4 shows the internal components and how they are arranged within the cabinet or housing. As can be easily seen, the front panel 40 and rear panel 42 support most of the components. The side panels 46 and 48 make up the remaining portion of the outer perimeter of the structure. The power switch 54 and test switch 56 are mounted on the front panel 40. The sensitivity control knob 60 is mounted on a suitable shaft 66 which is positioned within a hole provided in the panel 40 and secured with a bushing and retaining nut 68. Mounted on the opposite end of the shaft 66 is a cylindrically-shaped control 70 having an inclined cam surface 72. The hollow tube connector 58 is mounted on the front panel by means of a shoulder and threaded retaining nut 74 with an interconnected, sealed, flexible bellows 76 provided on the opposite side. The bellows or pneumatic actuator 76 can be made from any flexible, gas impermeable material such as thin plastic or synthetic rubber. It is necessary that the actuation bellows be manufactured from a relatively thin material so that even slight variations in pressure will be sensed as extensions or retractions along the longitudinal axis of the bellows as shown by the arrow in FIG. 5. An actuation push rod 78 is mounted in the end of the bellows for moving the electrical contacts which will be explained later.

The speaker 62 and phone jack 64 are mounted on the back panel 42. A printed circuit board 80 is mounted within the cabinet and can be arranged as shown in the corner between the side panel 48 and back panel 42. All of the electronic components and their interconnecting circuitry is provided on the circuit board 80. A suitable bracket or mounting plate can be provided above or below the components just described and within the cabinet for mounting of the battery power source. Also, suitable interconnecting wiring connecting the circuit board 80 with the various major components such as switches, jacks, and speaker, are suitably provided.

The most critical area of the invention lies in conjunction with the actuation bellows 76. A bracket 82 is suitably positioned with respect to the bellows and includes an electrical switch unit 84 mounted thereon. The electrical switch unit 84 includes a sub-bracket 86 mounted on the housing bracket 82 with an elongated arm 88 pivotally mounted by hinge 90 on the sub-bracket 86. The outward end of the mounting arm 88 includes an angularly bent follower portion 92 which is suitably adjusted so that the end 92 rides in proper position on the cam surface 72.

Mounted on the arm 88 is switch block 94 having stationary electrical contact 96 and moveable contact 98. A push rod 100 is positioned between the moveable contacts 98 so that they will move in unison. Any number of pairs of moveable contacts 98 and stationary contacts 96 to perform electrical switching functions can be provided. At least one pair 97 is provided and connected to the electronic circuitry within the cabinet to provide the internal alarm signal which is included as part of this patient call system. Auxiliary or additional pairs 99 of contacts can be provided and electrically connected to the phone jack 64 or a plurality of these jacks to provide actuation of various external or remote alarm or patient call systems. A spring biasing device 102 such as the helical spring shown in FIG. 5 is positioned between the bracket 82 and the arm 88 to provide a constant biasing force on the switch moveable contacts 98 and the cam follower end 92. Thus, the cam follower 92 is always held against the cam surface 72 with the outer moveable contact 98 always held in position against the end of the actuation bellows push rod 78.

If desired, the moveable switch contacts 98 can be suitably bent or positioned to adjust the actual force placed on the bellows push rod 78 and bellows 76 as well as the actuation distance required for movement of the contacts 98 before electrical contact is made with the stationary contact 96. In addition, the cam surface 72 can be slightly serrated or incorporate a plurality of detent notches (not shown) which can hold the cam position with respect to the follower end 92. In this way the sensitivity adjustment will not shift even with subjecting the housing to movement or vibration. Also by strategically locating detent notches on the cam surface, it is possible to preset the sensitivity for a known patient condition.

Figure 6:
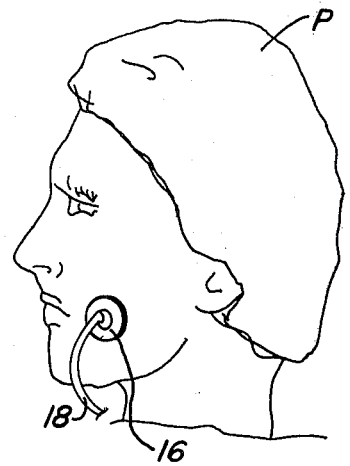
FIG. 6 is a pictorial view showing the transducer mounted on the patient's cheek where it can be actuated.
Figure 9:
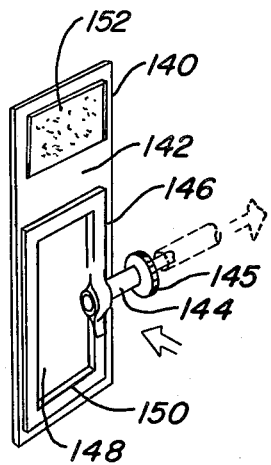
FIG. 9 is a perspective view showing the patient side of an elongated strip-type transducer having a side tube connection and arranged so that the strip can be wrapped around a portion of the patient's body.

A hose 18 of suitable length has one end attached to the tube connector 58 and the bellows 76. The opposite end of the hose is connected to an open patient transducer 16. As shown in FIG. 6, the transducer can be mounted directly on the skin of the patient P in any location which is near or adjacent to an area where there is voluntary muscular control. Thus, by even slight muscular movement, the skin adjacent to the transducer 16 can be moved to pressurize the system sufficiently to actuate the electrical contacts and produce an alarm signal.

Figure 8:
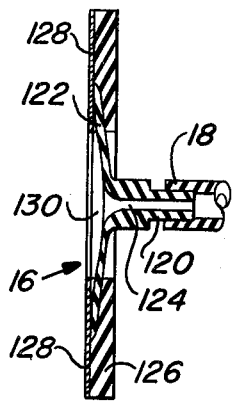
FIG. 8 is a cross-section of the patient transducer taken along the lines 8—8 of FIG. 7.

FIGS. 7 and 8 show a typical patient transducer 16 which includes a hose connector 120 to which the hose 18 is coupled. A generally planar surface member 122 to which the hose connector 120 is attached. A hollow passage 124 communicates from the open side of the member 122 to the interior of the hose 18. The outside diameter of the hose coupling 120 is slightly larger than the interior diameter of the hose 18 to provide a sealed or air tight coupling between the hose and transducer 16. It is also worthwhile to note that the tube 18 can be any common type of plastic hose or any other type of material which is inherently non-conductive gas impermeable and will transmit an increase in pressure to the actuating bellows 76. It has been found that intravenous tubing which is common in hospitals works satisfactorily with this device.

The outer perimeter configuration of the member 122 can be of any shape, but it has been found that a circular configuration works satisfactorily. Around the outer edge of the member 122 can be positioned a plastic, non-porous sponge ring 126 which is shaped to fit and accept the outer edges of the member 122. A suitable arrangement is provided around the outer perimeter and surface of the member 122 and ring 126 to seal the member 122 against the surface or skin of the patient's body. Shown in FIG. 8 is an adhesive material 128 which is pressure sensitive and provided on the generally flat surface of the ring 126 and perimeter of the member 122. A cover sheet can be provided to cover the adhesive material 128 which can be easily peeled away prior to the application of the transducer on the skin of the patient.

An at least slight volume cavity 130 is provided along the surface to which the hose connection 120 is made. Thus, as can be seen, slight movement in the position of the skin by any available voluntary muscular control of the patient will decrease the volume within the cavity 130 which is sufficient to slightly increase the pressure within the patient transducer 16, tube 18 and actuation bellows 76. Depending upon the sensitivity to which the switch unit 84 is adjusted, this pressure should be sufficient to cause the moveable contacts 98 to contact the stationary contacts 96 causing the closing of the electric circuits. This closing of the electric contacts causes the electronic circuitry to be energized producing an audible sound which is produced by the speaker 62. Simultaneously the auxiliary contacts can also energize a remote alarm signal which can be of any type to notify or warn other persons of the patient's needs.

In operation, the sensitivity of the actuation bellows device 76 and the switch unit 84 is controlled by the sensitivity knob 60 and rotatable cylinder 70. By rotating the knob 60, the cam surface 72 is moved either towards or away from the follower 92 portion of the mounting arm 88. When the arm 88 is moved against the spring pressure, the moveable contacts 98 of the switch unit 84 are moved away from the actuation bellows 76 reducing the force applied to the push rod 78. by rotating the knob 60 in the opposite direction, the follower 92 moves toward the left or knob position as shown in FIG. 5 which allows the spring 102 to expand against the arm 88. In this way the moveable contact arms 98 of the switch unit 84 are allowed to increase force on the push rod 78 and the actuation bellows 76. In this way less differential pressure change is required in the actuation bellows 76 to cause the contacts 98 to make the electrical circuit against the stationary contacts 96. In this way the sensitivity or pressure differential in the pneumatic portion of the unit can be precisely adjusted so that only very slight skin movement by the patient will be sufficient to actuate the call device.

It is also possible by changing the length of the interconnecting rod 100 between the various moveable switch contacts 98 different pressure actuation requirements can be provided for various pairs of electrical contacts. Thus, slight movement within the bellows 76 and push member 78 will cause a first set of contacts 97 to actuate without the second or additional contacts making the circuit. Additional pressure or movement of the push rod 78 in the longitudinal direction towards the contacts will then cause the additional contacts to close their respective electrical circuit. Thus, by increasing the pressure, the various circuits when made in turn, can designate the needs of the patient. Thus, the first contacts can merely identify the necessity of a call or attention to the patient while a second or additional contacts can indicate an emergency situation.

Another embodiment of the open patient transducer 16 which can be utilized with the present invention is the strip-like transducer 140. An elongated body sheet 142 is provided which has an elongated tube pipe or connector 144. One end of the tube 144 is welded or heat sealed along the inner side 148 of the strip 142 so that the open end of the tube 144 is adjacent to the inner surface 148. A gripping ring 145 can be provided on the tube to facilitate handling, and the opposite end of the tube 144 can be reduced in diameter to fit the inside diameter of the tube 18. A gasket 146 can be provided in a continuous or closed fashion around the inner surface 148 of the transducer 140 to define an area which is contiguous with the inner end of the tube 144. This gasket material 146 can be of plastic sponge or other generally impervious material which will seal around the edges of the strip and against the body of the patient and substantially prevent the escape of gas trapped within the gasket area. An adhesive material 152 can be provided at the end of the strip outside of the gasket area as one way of holding the strip on the body of the patient.

With this type of transducer 140, the strip 142 can be wrapped around the wrist, thigh, bicep, or other portion of the patient's body whereby slight voluntary muscular movement will reduce the volume of the cavity 150 provided between the strip 142 and the patient's skin. In this way pressure within the cavity 150 and the pneumatic portion of the device will be increased sufficiently to activate the actuation bellows and switch contacts. It is to be understood that the adhesive area 152 can be provided to adhere to the outer surface of the strip 142 when the strip is completely wrapped around the body portion of the patient. Any other means of attaching the strip to the body portion can be utilized such as applying the adhesive to the surface of the gasket 146 to cause the gasket itself to adhere the strip 142 to the patient's body. It is also possible that other means of fastening or mounting the strip to the patient's body can be provided such as ties or the use of adhesive tape to actually tape the strip 142 to the patient's body.

Figure 10:
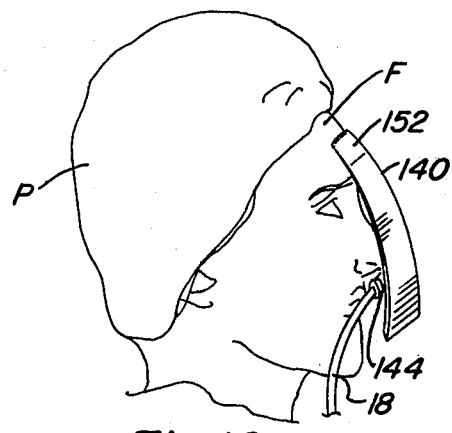
FIG. 10 is a pictorial presentation of another embodiment of a patient transducer according to the present invention which shows the transducer mounted in front of the lips of the patient whereby exhalation can actuate the call device.

Still another embodiment of the open patient transducer 16 can be provided as shown in FIG. 10. In this arrangement, the strip transducer 140, as described above, can be used with the adhesive area 152 attached to the patient's forehead F in a particular area so that the inner end of the tube 144 is positioned adjacent to the nostrils or in front of the lips of the patient P. Merely exhaling or blowing the breath against the open end of the tube will be sufficient depending upon the sensitivity adjustment of the unit to activate the alarm device. In this way the transducer can move with the patient and will be strategically located in front of the lips or nostril. Also, there is the possibility that the tube 18 without the use of a transducer can be inserted within a nostril of the patient so that sudden exhalation will activate the system.

As an alternative, an open patient transducer similar to the transducer that is shown in FIG. 7, but having a more pronounced cone or funnel shape, can be utilized which is positioned on an adjustable bracket (not shown) supported from a portion of the bed frame which moves with the patient. This transducer can be positioned in front of the mouth or nose of the patient to be activated by the exhalation.

Figure 11:
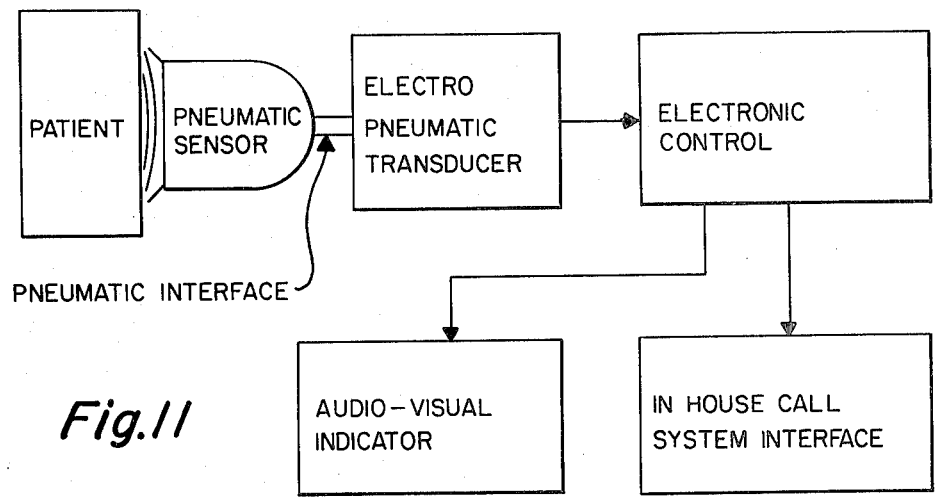
FIG. 11 is a block diagram showing the basic operation of the present invention.

FIG. 11 shows a block diagram of the patient call device as provided in the present invention. This diagram shows the basic operation of the device with the patient transducer or pneumatic sensor mounted on or adjacent to the patient whereby the patient can exercise some control over minute pressure changes within the transducer. As previously described, this can be by the transducer being directly adhered to a body surface of the patient whereby slight muscular movement will increase the pressure within system or the pressure can be increased by blowing or exhaling into the transducer. This pressure increase is transmitted through the pneumatic interface to the actuation transducer or bellows whereby the increase in pressure is sensed mechanically through the extension of the bellows. This transfer of mechanical movement energizes one or more pairs of electrical contacts either simultaneously or in sequence. The actuation point and pressure requirements for energizing the electrical contacts is minutely adjusted to provide the desired sensitivity.

Usually the first pair of contacts actuated will be connected to the electronic control circuitry provided within the device. This circuitry draws no current in a stand-by position until the contacts are actuated. In this way an audio oscillator is activated with a predetermined frequency and characteristic sound provided by an internal speaker to alert persons to the needs of the patient. By the same token, the electronic control portion of the present invention can activate one or more additional pairs of electrical contacts which can be directly connected to auxiliary alarm systems such as those provided in a hospital nurse call system. Other pairs of contacts can be connected to such things as an automatic dialing device, other equipment or appliances such as television, controls for the bed operation, etc. There is also the possibility that the actual audible alarm can be provided on the second or even third pair of contacts actuated so that the preliminary contacts can control operation of the equipment or appliances.

Figure 12:
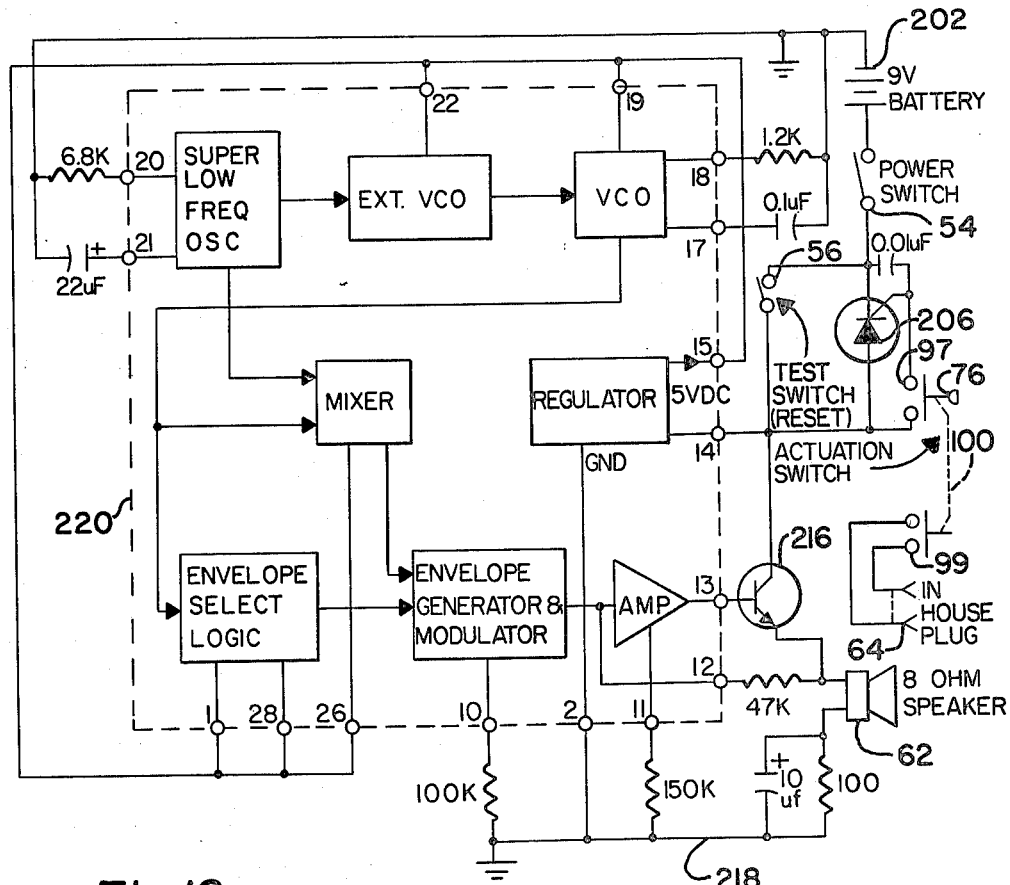
FIG. 12 is a schematic diagram showing an electrical circuit for the present invention.

FIG. 12 shows a typical electronic circuit which can be utilized in the functioning of the patient call system according to the present invention, to provide the audible alarm signal. Throughout this description, reference will be made to actual values for the external components. These values have been found due to experimentation to be satisfactory for producing the desired results.

Electrical energy is provided by a battery power source 202 which can be of a 9-volt type. The positive side of the battery 202 is connected through power switch 204 to the cathode of a silicon-controlled rectifier (SCR) 206. A capacitor 208 shunts the gate of the SCR to the cathode. One set of contacts 97 connected to the actuation bellows 76 connect the gate to the anode. A reset-test switch 56 is provided to by-pass the silicon-control rectifier 206 to test the operability of the alarm circuit. An auxiliary pair of electrical contacts 99 are provided in conjunction with the actuation bellows 76 and are arranged so that they make contact simultaneously with the contacts 97 or in sequence as desired.

The contacts 99 can be connected to an auxiliary call system in-house jack or plug 64.

The anode of silicon-controlled rectifier 206 is connected to the emitter of an npn transistor 216 while at the same time it is connected to one lead of a voltage regulator circuit. The regulator is grounded through pin 2 to the negative voltage bus 218. The output of the regulator through pin 15 supplies a regulated +5 v DC to the VCO at pin 19, the external VCO at pin 22, the envelope select logic through pins 1 and 28 and the mixer through pin 26. Negative 9 volts is provided to power the VCO through a 1.2 K resistor and a 0.1 uf input capacitor. Negative battery voltage is also simultaneously applied to the super low frequency oscillator (SLFO) through a 6.8 K resistor and 22 uf capacitor. By the same token, negative battery voltage is applied through a 150 K resistor to the OPERATIONAL AMPLIFIER and a 100 K resistor through pin 10 which controls the amplitude of the wave form generated.

An output from the SLFO is fed to the VCO through an external VCO with the output from the VCO fed both to a mixer and an envelope select logic circuit. A second output from the SLFO is also fed to the mixer. The envelope generator and modulator is fed by an output from both the mixer and the logic select circuit with the output from the modulator fed to the OP AMP. An audio frequency signal is fed to the base of the audio output transistor 216. The collector is connected to one side of the speaker 62 and feedback is provided to the input of the OP AMP through a 47 K resistor from the emitter of the transistor. The speaker is connected to the negative side of the power source through a 100 ohm current limiting resistor and a 10 microfarad capacitor.

The speaker as shown in FIG. 12 can be an 8 ohm speaker which essentially matches the output impedence of the audio output transistor 216. By closing the contacts 97 by means of the patient actuation of the pneumatic portion of the control device, the silicon-controlled rectifier switch 206 places current on the voltage regulator and the audio transistor 216. The application of a high voltage input from the regulator to the VCO and the logic circuits causes a chopped or chirping audio frequency to be generated through the mixer and modulator to the input of the OP AMP. The output of the OP AMP controls the function of the audio output transistor 216 to cause the speaker to generate a distinctive audible alarm signal.

The components and circuit shown within the dotted line 220 as provided in FIG. 12 can be provided in a conventional solid-state, integrated circuit device. A typical integrated circuit device of this nature would be a complex sound generator, such as a type SN 75477 integrated circuit, produced by Texas Instruments Inc. The pin designation shown in FIG. 12 are for this device. The units for the additional electronic components shown in FIG. 12 have been found to be suitable to provide an audio signal of varying frequency. Any type of audio frequency generator which will provide a distinctive alarm signal can be utilized with the present invention.

Although the patient call device which is shown and described in the present invention has been used with paraplegic, partially paralyzed or handicapped patients, there is also the possibility that this device can be used in other applications. Some of these might be in industrial use to sense minor pressure increases or differentials as a signaling or warning device. Other areas might be in burglar alarm or intruder sensors wherein inadvertent movement close to the sensing transducer would be sufficient to increase the pressure in the pneumatic portion to set off an alarm. In this type of device it is possible that only the remote alarm contacts would be utilized.

Through experimental use of the hereindescribed patient call device, it has been found that an increase in pressure in the patient transducer and pneumatic portion of the device of as little as 3 to 5 grams is sufficient to actuate the alarm signal. Through the adjustment of the sensitivity control, it is possible to adjust the pressure required to actuate the system from 3 to 5 grams to as much as 1 kilogram. The attendant or nurse can select the type of patient transducer which will best suit the individual patient and his capabilities. After selection of the proper transducer and the attachment of the transducer to a strategic location on the patient, the sensitivity control and the actuation point can be adjusted by turning on the electrical power and adjusting the knob until proper actuation sensitivity is obtained. Thus, a wide variety of applications in patient use can be obtained through the use of the present invention.

While a new and novel patient call system has been shown and described in detail, it is to be understood that this invention is not to be considered to be limited to the exact form disclosed in that changes in detail and construction may be made therein within the scope of this invention without departing from the spirit thereof.

What is claimed is:

1. A self-contained, electrically isolated patient call device which can be used by a patient having limited muscular movement, said device comprising:
    a battery energy power source which is of low voltage to prevent electrical shock;
    electrical switch means arranged in conjunction with a pneumatic actuation means which permits the making and breaking of electrical contacts in response to the movement of said pneumatic means;
    means for positioningly adjusting the relationship of the switch means with respect to said pneumatic means whereby the sensitivity of the actuation of said switch means with the movement of the pneumatic means can be precisely adjusted;
    alarm means connected to said electrical switch means and powered by said battery power source whereby when said contacts are made, an alarm signal is generated for alerting persons to the needs of said patient; and
    an open pneumatic transducer means arranged in juxtiposition to a portion of the patient's body and connected by a tube means to said pneumatic actuation means whereby a minor muscular movement by said patient will cause the pneumatic actuation means to energize said contact means to produce said alarm signal.

2. A patient call device as defined in claim 1 wherein said open pneumatic transducer means is mounted adjacent to the surface of said patient's body whereby slight movement of the patient's body will cause a pressure increase in the transducer means which will cause the pneumatic actuation means to energize said switch means.

3. A patient call device as defined in claim 1 wherein said pneumatic transducer means has a generally flat surface member which includes a means for connecting said tube means and the opposite side of said surface member has means for attaching the transducer means to the patient's body to form a pneumatically closed system whereby slight changes in the volume between the patient's body and the surface of said member will cause an increase in pressure within the tube means and pneumatic actuation means which will be sufficient to energize said contact means.

4. A patient call device as defined in claim 3 wherein the perimeter of said member on the opposite surface of said tube connection includes an adhesive means to adhere and seal said surface on the skin of the patient.

5. A patient call device as defined in claim 3 wherein the surface of said member opposite said tube connection is positioned adjacent to the lips of said patient whereby exhalation by the patient will create sufficient pressure to actuate said pneumatic actuating means whereby said alarm means will be energized.

6. A patient call device as defined in claim 1 wherein said open pneumatic transducer means is a band of material which can be wrapped around a portion of the patient's body, said material including means for sealing the edge of the material at the surface of said patient's body whereby slight movement of the body adjacent to said material will effectively reduce the volume within the transducer means which will slightly increase the pressure in said pneumatic actuation means sufficiently to actuate said electrical contacts.

7. A patient call device as defined in claim 1 wherein said alarm signal is an audible sound.

8. A patient call device as defined in claim 7 wherein said audible sound is of a continuously varying frequency to produce a distinctive sound signaling the needs of said patient.

9. A patient call device as defined in claim 1 which further includes at least two pairs of electrical contacts in conjunction with said electrical switch means whereby a remote second alarm means can be energized simultaneously for alerting remote persons to the needs of said patient.

10. A patient call device as defined in claim 1 wherein said switch adjusting means includes a rotatable, cylindrical cam surface whereby rotation of the cam surface dimensionally adjusts the switch contact means with respect to said pneumatic means, said cam surface having relatively small longitudinal dimensional change in relation to angular rotation whereby the position of said electrical contacts can be precisely adjusted.

11. A patient call device as defined in claim 1 wherein said electrical switch means is arranged whereby additional longitudinal movement of said pneumatic actuation means will energize additional electrical contacts whereby the patient can indicate the type of need or urgency that is required.

12. A self-contained, electrically-isolated, patient call device which is intended for use with substantially paralyzed patients, said device comprising:
    a battery power source,
    an alarm means powered by said battery power source which can produce a distinguished alarm signal indicating the needs of said patient;
    means for energizing the alarm means,
    pneumatic actuation means which includes adjusting means for varying the dimensional position of said energizing means with respect to said actuation means for varying the sensitivity of said energizing means,
    open transducer means mounted on the skin of said patient in an area which can be flexed by at least limited voluntary muscular control, and tube means interconnecting said pneumatic actuation means and said open transducer means to form a pneumatic system whereby the slight flexing of the skin surface of said patient will increase the pressure within said transducer means sufficiently to extend the pneumatic actuation means and activate said alarm energizing means.

13. A patient call device as defined in claim 12 wherein said alarm means further includes means for actuating at least one additional remote alarm means simultaneously with the first alarm means.

* * * * *